(12) United States Patent
Gharda et al.

(10) Patent No.: US 7,777,052 B2
(45) Date of Patent: Aug. 17, 2010

(54) PROCESS FOR THE PREPARATION OF FIPRONIL, AN INSECTICIDE, AND RELATED PYRAZOLES

(75) Inventors: Keki Hormusji Gharda, Mumbai (IN); Ashokkumar Maganlal Malte, Thane (IN); Pulinattu Cherian Joseph, Thane (IN); Sureshkumar Dattatraya Parkar, Ambarnath (IN); Shekhar Vishwanath Sathe, Dombivli (IN); Pragnesh Dalpatram Damania, Mumbai (IN)

(73) Assignee: Gharda Chemicals Limited, Dombivli, Maharashtra, IN (US)

( * ) Notice: Subject to any disclaimer, the term of this patent is extended or adjusted under 35 U.S.C. 154(b) by 275 days.

(21) Appl. No.: 12/086,359

(22) PCT Filed: Apr. 25, 2006

(86) PCT No.: PCT/IB2006/000999

§ 371 (c)(1),
(2), (4) Date: Jun. 11, 2008

(87) PCT Pub. No.: WO2007/122440

PCT Pub. Date: Nov. 1, 2007

(65) Prior Publication Data

US 2009/0030211 A1 Jan. 29, 2009

(51) Int. Cl.
*C07D 231/44* (2006.01)
(52) U.S. Cl. .................................................. 548/367.7
(58) Field of Classification Search ........................ None
See application file for complete search history.

(56) References Cited

FOREIGN PATENT DOCUMENTS

| EP | 295117 | 12/1988 |
|---|---|---|
| WO | WO 01/30760 | 5/2001 |

OTHER PUBLICATIONS

Barton, D. H. R. et al, "Tetrahedron Lett.", 1982, vol. 23, No. 9, pp. 957-960, XP002417809. (ISR).
Written Opinion of the International Searching Authority, 2007.
International Search Report, 2007.
Barton, D. H. R. et al, "Observations on the Chemistry of the Iodoxy Group", Tetrahedron Letters, 1982, vol. 23, No. 9, pp. 957-960. (ISR).

Primary Examiner—Kamal A Saeed
(74) Attorney, Agent, or Firm—Collard & Roe, P.C.

(57) ABSTRACT

This invention relates to a process for the preparation of 5-amino-1-phenyl-3-cyano-4-trifluoromethyl sulphinyl pyrazoles as defined by Formula-I,

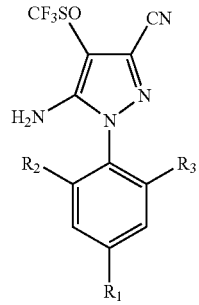

(Formula-I)

wherein: R1=trifluoromethyl or trifluoromethoxy, and R2, R3=individually hydrogen, chlorine or bromine, the process comprising the step of oxidizing a compound of Formula-II,

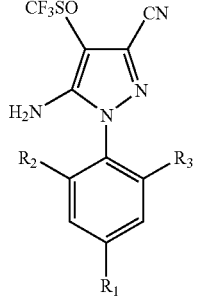

(Formula-II)

wherein: R1=trifluoromethyl or trifluoromethoxy, and R2, R3=individually hydrogen, chlorine or bromine, in a medium comprising at least one oxidizing agent and trichloro acetic acid, and/or the reactions product (s) of the at least one oxidizing agent and trichloro acetic acid, and at least one melting point depressant. The preferred pyrazole is Fipronil, preferably prepared using hydrogen peroxide and dichloro acetic acid at room temperature.

15 Claims, No Drawings

PROCESS FOR THE PREPARATION OF FIPRONIL, AN INSECTICIDE, AND RELATED PYRAZOLES

CROSS REFERENCE TO RELATED APPLICATIONS

This application is the National Stage of PCT/IB2006/000999 filed on Apr. 25, 2006, which claims priority under 35 U.S.C. §119 of PCT/IB2006/000999 filed on Apr. 25, 2006. The international application under PCT article 21(2) was published in English.

BACKGROUND OF THE INVENTION

This invention relates to the preparation of 5-amino-1-phenyl-3-cyano-4-trifluoromethyl sulphinyl pyrazole pesticides as defined by formula-I below, and in particular to 5-amino-1-(2,6-dichloro-4-trifluoromethylphenyl)-3-cyano-4-trifluoromethyl sulphinyl pyrazole. This pesticide, known as Fipronil, titled in Pesticide Manual, 13$^{th}$ edition, entry No. 354, is an important insecticide and was invented by Rhone Poulenc (now BASF AG) in 1987.

The known commercial process for the manufacture of this compound uses corrosive and expensive chemicals such as trifluoro acetic acid. This process needs considerable improvement to make it economically viable. Research for an alternative has led to the invention disclosed herein.

SUMMARY OF THE INVENTION

The main object of the present invention is successfully to substitute the corrosive and expensive solvent trifluoro acetic acid with an inexpensive and easily available but effective alternative solvent. Although the structurally related compound trichloro acetic acid was initially considered to be unsuitable because it is not a liquid at room temperature, it has been found that this compound can be made to be an effective solvent in the proposed manufacturing process through the use of a compatible melting point depressant which does not adversely affect the process, such as monochloro acetic acid, dichloro acetic acid, methylene dichloride, ethylene dichloride, monochlorobenzene or a haloalkane.

The present invention relates to an improved process of oxidation of 5-amino-1-phenyl-3-cyano-4-trifluoromethyl sulphinyl pyrazoles using an oxidizing agent, preferably hydrogen peroxide, in a medium comprising trichloro acetic acid as a substitute for the hitherto used expensive and corrosive trifluoro acetic acid solvent.

Overall, the invention makes the commercial manufacture of the important insecticide Fipronil more process friendly and economically viable.

DESCRIPTION OF THE INVENTION

The present invention relates to improved oxidation process for preparing 5-amino-1-phenyl-3-cyano-4-trifluoromethyl sulphinyl pyrazole pesticides as defined by formula-I below.

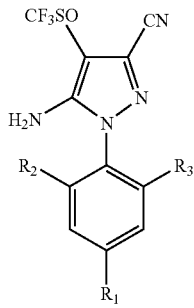

(Formula-I)

Wherein,

R1=trifluoromethyl or trifluoromethoxy

R2, R3=individually hydrogen, chlorine or bromine which process comprises the step of oxidizing a compound of formula-II.

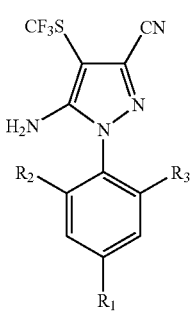

(Formula-II)

Wherein,

R1=trifluoromethyl or trifluoromethoxy

R2, R3=individually hydrogen, chlorine or bromine by using a medium comprising at least one oxidizing agent and trichloro acetic acid, and/or the reaction product(s) of the at least one oxidizing agent and trichloro acetic acid, and at least one melting point depressant. The presence of trifluoro acetic acid (TFA) is thereby rendered unnecessary. The preferred oxidizing agents are per acids, peroxides and persulfates. More preferred are peroxides, in particular benzoyl peroxide, sodium peroxide, tert butyl peroxide and hydrogen peroxide, the most preferred oxidizing agent being hydrogen peroxide. Hydrogen peroxide may be used in the form of a concentrated aqueous solution such as those that are available commercially.

European patent No. 295117 describes the preparation of compounds of formula-I using 3-chloroperbenzoic acid, but not using the oxidation route of the present invention.

WO 01/30760 describes a process for the oxidation of compounds of formula-II to compounds of formula-I in a trifluoro acetic acid medium using a corrosion inhibitor as an improvement to take care of the acidity generated due to the liberation of hydrofluoric acid (HF) during the reaction.

Oxidation of compounds of the type of formula-II entails several difficulties, for example that the molecule has to be stable under the conditions of oxidation, the oxidation should proceed to the desired level without leaving significant starting materials unreacted and the oxidation should not produce an excessive level of sulfonyl derivative. Oxidants such as per acids, peroxides, and persulfates have been widely used for performing such oxidation reactions.

The oxidation reaction is conventionally carried out in organic solvents, particularly halogenated aliphatics, trifluoroacetic acid. Mineral acids are generally not useful as a medium for oxidation due to the instability of the compounds of the invention towards strong mineral acids.

Trifluoro acetic acid has been reported to be a good medium for effecting the oxidation, with good conversion and selectivity to the sulphinyl derivative with minimum levels of sulphonyl derivative formation. However, trichloro acetic acid has not been reported as a medium due to its high melting point.

DETAILED DESCRIPTION OF THE INVENTION

Several process problems are encountered when trifluoro acetic acid (TFA) is used as a solvent. One major problem is the corrosion of metal or glass equipment due to the liberation of HF during the reaction. WO 01/30760 describes how the addition of corrosion inhibiting agents such as boric acid can be used to prevent this. Whilst this may be effective during oxidation, since TFA is a costly chemical it needs to be recovered due to process economics. The same patent application discloses the addition of monochloro benzene and distillation of TFA. Further, residual TFA is esterified using alcohol and recovered as an ester which needs to be converted back to TFA. Moreover, the TFA is distilled out as an azeotrope with water and separation of pure TFA from water requires distillation with sulfuric acid addition. This again poses severe corrosion problems to the equipment used. In short, the use of TFA makes the commercial operation of the process extremely difficult and expensive.

Our research has now led to a solution to this knotty problem and has made the process simple and economical. Our search for a substitute for TFA led to the present invention of using trichloro acetic acid.

The process of the present invention involves the preparation of a compound of formula-I by a process comprising the step of oxidizing a compound of formula-II. The oxidation is carried out in a medium comprising at least one oxidizing agent and trichloro acetic acid, and/or the reaction product(s) of the at least one oxidizing agent and trichloro acetic acid, and at least one melting point depressant.

Since trichloro acetic acid is a solid under the conditions of oxidation, at least one melting point depressant is required. Preferred melting point depressants are dichloro acetic acid, monochloro acetic acid, methylene dichloride, ethylene dichloride, monochlorobenzene or a haloalkane, or a mixture thereof. Trichloro acetic acid is commercially available at about one tenth the cost of Trifluoro acetic acid and is devoid of the corrosion problems arising due to HF. The use of corrosion inhibitors such as boric acid and the consequential processing problems that they create are therefore avoided. The present invention seeks to provide an industrial process for manufacturing compounds of formula-I, particularly Fipronil, in high yield and purity with cheaper and less corrosive chemicals.

Furthermore, the present invention seeks to provide a process for manufacturing the compounds of formula-I, particularly Fipronil, using chemicals which do not corrode the equipment used.

The preferred oxidizing agents are per acids, peroxides and persulfates, with peroxides being particularly preferred. The preferred peroxides are benzoyl peroxide, sodium peroxide, hydrogen peroxide and tert butyl peroxide. The preferred per acid is per acetic acid. The most preferred oxidizing agent is hydrogen peroxide.

The quantity of the oxidizing agent used is sufficient to effect optimal conversion of the compound of formula-II to the compound of formula-I without producing significant amounts of the byproduct sulphonyl derivative. For the peroxides such as hydrogen peroxide this is preferably in the range of 1.1 to 1.7 moles, and more preferably about 1.4 mole, per mole of the compound of formula-II. The preferred concentration of the hydrogen peroxide used is 50 to 70% by weight as an aqueous solution due to the commercial availability of such solutions. Concentrations outside this range can also be used with suitable adjustments to the water concentration.

In a preferred embodiment of the process, trichloro per acetic acid, which is the reactive species, is formed 'in situ' by contacting hydrogen peroxide with trichloro acetic acid. Other oxidizing agents such as tert butyl hydrogen peroxide and per acetic acid can also be used, but with no particular advantage. For those skilled in the art, Trichloro per acetic acid can be pre-made and used, but there is no particular advantage in doing so.

The temperature for the reaction is chosen so as to give reasonable kinetics for oxidation without decomposing the product. The reaction is preferably carried out at a temperature in the range 0° C. to 50° C., more preferably in the range 15 to 25° C. and most preferably at about 20° C.

The quantity of trichloro acetic acid used should generally be sufficient to dissolve the substrate and allow the slurry of the reaction mass to be stirred properly. Preferably 1.0 lt to 2.0 lt of trichloro acetic acid is used per mole of the compound of formula-II. The composition of the mixture is chosen so as to depress the melting point of the reaction medium sufficiently, usually to less than 10° C. For example, the preferred melting point depressant dichloro acetic acid is a poor medium for oxidation and the purpose of its addition is only to sufficiently depress the melting point of trichloro acetic acid to facilitate ease of processing. 20-30% by weight content of dichloro acetic acid in the trichloro acetic acid is generally sufficient to achieve this objective. It is preferred to depress the melting point of the trichloro acetic acid to below 10° C.

In a preferred embodiment of the process of the present invention R1=trifluoromethyl and R2, R3=chlorine, the process therefore resulting in the production of 5-amino-1-(2,6-dichloro-4-trifluoromethylphenyl)-3-cyano-4-trifluoromethyl sulphinyl pyrazole (Fipronil).

The following examples, which are non-limiting, illustrate the invention:

Example 1

1000 ml of a solvent mixture, containing 700 ml trichloro acetic acid and 300 ml dichloro acetic acid, was added to a flask and 421 g (1 g mole) of 5-amino-1-(2,6-dichloro-4-trifluoromethylphenyl)-3-cyano-4-trifluoromethyl thio pyrazole was dissolved in it. After stirring for one hour at 20° C., 95 g hydrogen peroxide solution (50% w/w), equivalent to 1.4 mole, was added over a period of one hour. As the reaction proceeded, the solid product precipitated out from the reaction mass. The reaction was continued until the conversion was more than 95% as measured by HPLC. To the reaction mass, 2 litres of water was added, stirred and filtered. The water washed solids were dried in an oven at 110° C., resulting in 415 g solids (95% yield). HPLC determination by an internal standard method showed the solid to be 92% pure.

The filtrate portion was processed by distillation to recover the trichloro acetic acid using a conventional method and the trichloro acetic acid was recycled.

Example 2

1500 g of trichloro acetic acid solid was added to 300 ml of methylene dichloride. To this solution at 20° C., 421 g (1 g mole) of 5-amino-1-(2,6-dichloro-4-trifluoromethylphenyl)-3-cyano-4-trifluoromethyl thio pyrazole was added and allowed to dissolve. After stirring for 1 hour at 20° C., 93 g hydrogen peroxide solution (506 w/w), equivalent to 1.36 g mole, was added over a period of 2 hrs. The reaction was continued until the conversion was >95% using an HPLC area method. The excess hydrogen peroxide was destroyed using $Na_2SO_3$ and the solvent methylene dichloride was distilled out under a mild vacuum. To the residual mass, 2.0 lt water was added and the precipitated solids were filtered resulting in 410 g of buff coloured solids (yield: 93.8%). The solids were analyzed by an HPLC internal standard method and were found to be 92% pure.

The invention claimed is:

1. A process for the preparation of 5-amino-1-phenyl-3-cyano-4-trifluoromethyl sulphinyl pyrazoles as defined by Formula-I,

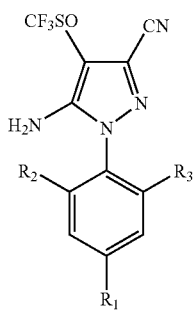

(Formula-I)

wherein: R1=trifluoromethyl or trifluoromethoxy, and
R2, R3=individually hydrogen, chlorine or bromine,
the process comprising the step of oxidizing a compound of Formula-II,

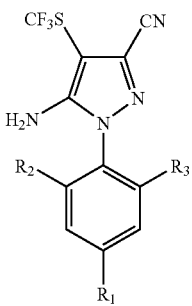

(Formula-II)

wherein: R1=trifluoromethyl or trifluoromethoxy, and
R2, R3=individually hydrogen, chlorine or bromine, in a medium comprising at least one oxidizing agent and trichloro acetic acid, and/or the reactions product(s) of the at least one oxidizing agent and trichloro acetic acid, and at least one melting point depressant.

2. A process as claimed in claim 1, wherein the at least one oxidizing agent is a per acid, a peroxide or a persulfate.

3. A process as claimed in claim 2, wherein the peroxide is hydrogen peroxide, tert butyl hydrogen peroxide, benzoyl peroxide or sodium peroxide.

4. A process as claimed in claim 3, wherein the hydrogen peroxide is used in an amount of between 1.1 and 1.7 moles per mole of the compound of formula-II.

5. A process as claimed in claim 4, wherein the hydrogen peroxide is used in an amount of about 1.4 moles per mole of the compound of formula-II.

6. A process as claimed in claim 3, wherein the hydrogen peroxide is added as a 50-70% by weight aqueous solution.

7. A process as claimed in claim 2, wherein the per acid is per acetic acid.

8. A process as claimed in claim 1, wherein the at least one melting point depressant is monochloro acetic acid, dichloro acetic acid, methylene dichloride, ethylene dichloride, monochlorobenzene or a haloalkane.

9. A process as claimed in claim 8, wherein the dichloro acetic acid is used in an amount of between 20% and 30% either w/w or v/v in the trichloroacetic acid.

10. A process as claimed in claim 1, wherein the process is carried out at a temperature in the range 0-50° C.

11. A process as claimed in claim 10, wherein the process is carried out at a temperature in the range 15-25° C.

12. A process as claimed in claim 11, wherein the process is carried out at a temperature of about 20° C.

13. A process as claimed in claim 1, wherein the at least one melting point depressant is used in such an amount as to depress the melting point of the reaction medium to less than 10° C.

14. A process as claimed in claim 1, wherein the trichloro acetic acid is used in an amount of between 1.0 liters and 2.0 liters per mole of the compound of formula-II.

15. A process as claimed in claim 1, wherein R1=trifluoromethyl and R2, R3=chlorine.

* * * * *

UNITED STATES PATENT AND TRADEMARK OFFICE
CERTIFICATE OF CORRECTION

PATENT NO. : 7,777,052 B2
APPLICATION NO. : 12/086359
DATED : August 17, 2010
INVENTOR(S) : Gharda et al.

Page 1 of 1

It is certified that error appears in the above-identified patent and that said Letters Patent is hereby corrected as shown below:

In particular, on the Title page, Item [73], change "IN (US)" to:    --India--.

On the cover page, Item [57], under the Abstract information, please change Formula II to correctly read as follows:

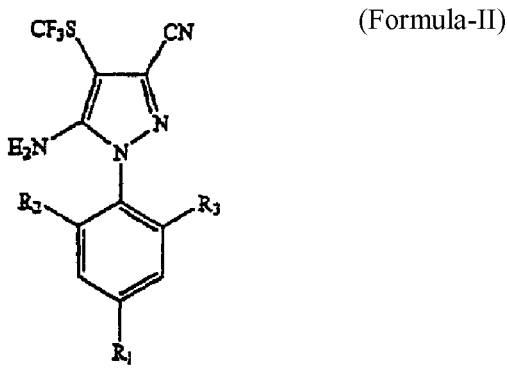

(Formula-II)

Signed and Sealed this

Twenty-third Day of November, 2010

David J. Kappos
*Director of the United States Patent and Trademark Office*